(12) United States Patent
Briggs (10) Patent No.: US 6,793,643 B1
(45) Date of Patent: Sep. 21, 2004

(54) LOW EXTRACORPOREAL VOLUME TREATMENT SYSTEM

(75) Inventor: Dennis A. Briggs, West Chester, PA (US)

(73) Assignee: Therakos, Inc., Exton, PA (US)

( * ) Notice: Subject to any disclaimer, the term of this patent is extended or adjusted under 35 U.S.C. 154(b) by 0 days.

(21) Appl. No.: 09/556,832

(22) Filed: Apr. 21, 2000

(51) Int. Cl.$^7$ .......................... A61M 37/00; C02F 1/00; C02F 1/38; B01D 15/00

(52) U.S. Cl. .................... 604/6.08; 604/5.01; 604/6.09; 604/6.01; 210/739; 210/782; 210/513

(58) Field of Search .............................. 604/5.01, 6.01, 604/19, 28, 65–67, 6.09, 6.1, 6.11, 6.08; 210/647, 739, 782, 101, 515

(56) References Cited

U.S. PATENT DOCUMENTS

| | | |
|---|---|---|
| 3,756,459 A | 9/1973 | Bannister et al. .............. 222/1 |
| 4,043,332 A | 8/1977 | Metcalf .................. 128/214 E |
| 4,048,994 A | 9/1977 | Lo ........................ 128/214 F |
| 4,132,644 A | 1/1979 | Kolberg ...................... 210/85 |
| 4,196,281 A | 4/1980 | Hearst et al. ................. 536/28 |
| 4,227,420 A | 10/1980 | Lamadrid ..................... 73/756 |
| 4,321,919 A | 3/1982 | Edelson ...................... 128/214 |
| 4,332,246 A | 6/1982 | Thomson ............... 128/214 F |
| 4,398,906 A | 8/1983 | Edelson .......................... 604/6 |
| 4,428,744 A | 1/1984 | Edelson .......................... 604/6 |
| 4,430,078 A | 2/1984 | Sprague ..................... 604/141 |
| 4,452,811 A | 6/1984 | della Valle .................. 424/281 |
| 4,464,166 A | 8/1984 | Edelson .......................... 604/6 |
| 4,464,354 A | 8/1984 | Bisagni et al. ................. 424/59 |
| 4,465,691 A | 8/1984 | Bisagni et al. ............... 424/256 |
| 4,469,593 A | 9/1984 | Ishihara et al. ............ 210/96.2 |
| 4,568,328 A * | 2/1986 | King ........................ 604/6.08 |
| 4,573,960 A | 3/1986 | Goss ............................. 604/6 |
| 4,573,961 A | 3/1986 | King ............................. 604/6 |
| 4,573,962 A | 3/1986 | Troutner ........................ 604/6 |

(List continued on next page.)

FOREIGN PATENT DOCUMENTS

| | | |
|---|---|---|
| EP | 0 094 682 | 11/1983 |
| EP | 0 284 409 | 9/1988 |
| EP | 0 611 228 | 8/1994 |
| EP | 0 704 224 | 4/1996 |
| WO | 93/14791 | 8/1993 |
| WO | 95/03814 | 2/1995 |
| WO | 97/36581 | 10/1997 |
| WO | 97/36634 | 10/1997 |
| WO | 97/37536 | 10/1997 |
| WO | 98/22163 | 5/1998 |
| WO | 98/22164 | 5/1998 |
| WO | 98/22165 | 5/1998 |
| WO | 98/22167 | 5/1998 |
| WO | WO 01/52009 | 7/2001 |

OTHER PUBLICATIONS

Barr et al., "Immunomodulation with Photopheresis: Clinical Results of the Multi–Center Cardiac Transplantation Study", one page.

(List continued on next page.)

*Primary Examiner*—Angela D. Sykes
*Assistant Examiner*—Leslie Deak
(74) *Attorney, Agent, or Firm*—Woodcock Washburn LLP (57) ABSTRACT

A means, apparatus, and system for reducing the net fluid volume deficiency in a patient during a medical treatment process. The invention seeks to modify a batch-type process to achieve the efficiency of a continuous process by precisely measuring the net change in fluid volume within a patient and dispensing the appropriate amount of biological fluids to a patient via IV lines or by recycling blood components into the patient while biological fluids are being withdrawn. The apparatus includes subcomponent lines, valving means, pumping means, load cells, storage chambers, a centrifuge, and centrifuge bowls. The system may have numerous feedback components to accurately measure and control the flow rates and amount of fluid dispensed to a patient.

49 Claims, 6 Drawing Sheets

U.S. PATENT DOCUMENTS

| | | | |
|---|---|---|---|
| 4,573,992 A | 3/1986 | Marx | 604/408 |
| 4,578,056 A | 3/1986 | King et al. | 604/6 |
| 4,582,598 A * | 4/1986 | Bilstad et al. | 210/101 |
| 4,586,920 A | 5/1986 | Peabody | 604/29 |
| 4,596,547 A | 6/1986 | Troutner | 604/4 |
| 4,600,401 A | 7/1986 | Kamen | 604/65 |
| 4,612,007 A | 9/1986 | Edelson | 604/5 |
| 4,613,322 A | 9/1986 | Edelson | 604/6 |
| 4,619,652 A | 10/1986 | Eckenhoff et al. | 604/415 |
| 4,623,328 A | 11/1986 | Hartranft | 604/4 |
| 4,642,088 A | 2/1987 | Guenter | 604/4 |
| 4,643,710 A | 2/1987 | Troutner | 494/60 |
| 4,657,160 A | 4/1987 | Woods et al. | 222/94 |
| 4,666,430 A | 5/1987 | Brown et al. | 604/141 |
| 4,681,568 A | 7/1987 | Troutner | 604/250 |
| 4,683,889 A | 8/1987 | Edelson | 128/395 |
| 4,684,521 A | 8/1987 | Edelson | 424/101 |
| 4,687,464 A | 8/1987 | Troutner | 604/4 |
| 4,692,138 A | 9/1987 | Troutner et al. | 604/4 |
| 4,693,981 A | 9/1987 | Wiesehahn et al. | 435/238 |
| 4,696,670 A | 9/1987 | Ohnishi et al. | 604/49 |
| 4,705,498 A | 11/1987 | Goss | 604/6 |
| 4,708,715 A | 11/1987 | Troutner et al. | 604/6 |
| 4,726,949 A | 2/1988 | Miripol et al. | 424/101 |
| 4,727,027 A | 2/1988 | Wiesehahn et al. | 435/173 |
| 4,737,140 A | 4/1988 | Lee et al. | 604/4 |
| 4,748,120 A | 5/1988 | Wiesehahn | 435/173 |
| 4,770,652 A * | 9/1988 | Mahurkar | 604/6.16 |
| D298,279 S | 10/1988 | Lee et al. | D24/51 |
| 4,778,451 A | 10/1988 | Kamen | 604/67 |
| D298,567 S | 11/1988 | Morris | D24/51 |
| D299,531 S | 1/1989 | Troutner et al. | D24/1.1 |
| D299,953 S | 2/1989 | King et al. | D24/1.1 |
| 4,808,161 A | 2/1989 | Kamen | 604/67 |
| 4,826,482 A | 5/1989 | Kamen | 604/67 |
| 4,838,852 A | 6/1989 | Edelson et al. | 604/4 |
| 4,866,282 A | 9/1989 | Miripol et al. | 250/455.1 |
| 4,897,789 A | 1/1990 | King et al. | 364/413.07 |
| 4,898,675 A * | 2/1990 | Lavender | 210/321.65 |
| 4,921,473 A | 5/1990 | Lee et al. | 494/27 |
| 4,952,812 A | 8/1990 | Miripol et al. | 250/455.1 |
| 4,955,860 A | 9/1990 | Ruano | 604/67 |
| 4,960,408 A | 10/1990 | Klainer et al. | 604/4 |
| 4,976,162 A | 12/1990 | Kamen | 73/865.9 |
| 4,976,707 A | 12/1990 | Bodicky et al. | 604/408 |
| 4,999,375 A | 3/1991 | Bachynsky et al. | 514/455 |
| 5,013,303 A | 5/1991 | Tamari et al. | 604/140 |
| 5,030,200 A | 7/1991 | Judy et al. | 604/5 |
| 5,088,515 A | 2/1992 | Kamen | 137/15 |
| 5,090,963 A | 2/1992 | Gross et al. | 604/132 |
| 5,106,374 A | 4/1992 | Apperson et al. | 604/140 |
| 5,147,289 A | 9/1992 | Edelson | 604/4 |
| 5,150,705 A | 9/1992 | Stinson | 128/396 |
| 5,163,909 A | 11/1992 | Stewart | 604/140 |
| 5,173,125 A | 12/1992 | Felding | 134/22 |
| 5,176,921 A | 1/1993 | Wiesehahn et al. | 424/529 |
| 5,178,182 A | 1/1993 | Kamen | 137/454.2 |
| 5,193,990 A | 3/1993 | Kamen et al. | 417/474 |
| 5,216,176 A | 6/1993 | Heindel et al. | 549/280 |
| 5,288,605 A | 2/1994 | Lin et al. | 435/902 |
| 5,308,309 A | 5/1994 | Morris | 494/85 |
| 5,330,420 A | 7/1994 | Lee | 604/4 |
| 5,344,568 A * | 9/1994 | Kitaevich et al. | 210/134 |
| 5,356,929 A | 10/1994 | Heindel et al. | 514/455 |
| 5,360,734 A | 11/1994 | Chapman et al. | 435/238 |
| 5,383,847 A | 1/1995 | Edelson | 604/6 |
| 5,399,166 A | 3/1995 | Laing | 604/146 |
| 5,401,342 A | 3/1995 | Vincent et al. | 156/73.1 |
| 5,417,346 A | 5/1995 | Ferri, Jr. et al. | 222/61 |
| 5,423,759 A | 6/1995 | Campbell | 604/153 |
| 5,433,738 A | 7/1995 | Stinson | 607/92 |
| 5,459,030 A | 10/1995 | Lin et al. | 435/2 |
| 5,459,322 A | 10/1995 | Warkentin | 250/455.11 |
| 5,482,193 A | 1/1996 | Fuchs | 222/633 |
| 5,482,828 A | 1/1996 | Lin et al. | 435/2 |
| 5,494,592 A * | 2/1996 | Latham et al. | 210/782 |
| 5,533,978 A | 7/1996 | Teirstein | 604/183 |
| 5,540,808 A | 7/1996 | Vincent et al. | 156/580.2 |
| 5,569,928 A | 10/1996 | Lee et al. | 250/494.1 |
| 5,578,005 A | 11/1996 | Sancoff et al. | 604/82 |
| 5,651,993 A | 7/1997 | Edelson et al. | 424/534 |
| 5,665,061 A | 9/1997 | Antwiler | 604/6.07 |
| 5,690,396 A | 11/1997 | Johnston et al. | 303/3 |
| 5,690,831 A * | 11/1997 | Kenley et al. | 210/645 |
| 5,700,245 A | 12/1997 | Sancoff et al. | 604/145 |
| 5,722,947 A | 3/1998 | Jeppsson et al. | 604/29 |
| 5,733,257 A | 3/1998 | Sternby | 604/27 |
| 5,776,104 A | 7/1998 | Guignard et al. | 604/132 |
| 5,779,666 A | 7/1998 | Teirstein | 604/52 |
| 5,785,681 A | 7/1998 | Indravudh | 604/65 |
| 5,791,370 A | 8/1998 | Harland | 137/340 |
| 5,792,367 A | 8/1998 | Mattisson et al. | 210/741 |
| 5,800,383 A | 9/1998 | Chandler et al. | 604/35 |
| 5,814,009 A | 9/1998 | Wheatman | 604/21 |
| 5,825,664 A | 10/1998 | Warrior et al. | 264/550 |
| 5,830,181 A | 11/1998 | Thornton | 604/102 |
| 5,843,037 A | 12/1998 | Uber, III | 604/151 |
| 5,853,397 A | 12/1998 | Shemesh et al. | 604/247 |
| 5,868,696 A | 2/1999 | Giesler et al. | 604/4 |
| 5,873,853 A | 2/1999 | Keilman et al. | 604/67 |
| 5,894,273 A | 4/1999 | Meador et al. | 340/606 |

OTHER PUBLICATIONS

Bisaccia et al., "Extracorporeal Photopheresis in the Treatment of AIDS–Related Complex: A Pilot Study," Ann. Int. Med. 113(4): 270 (1990).

Bisaccia et al., "Extracorporeal Photopheresis in the Treatment of AIDS–Related Complex: Extended Trial," J.AIDS 6: 386 (1993).

Campbell et al., "HCV RNA Peripheral Blood Mononuclear Cells of Chronic Hepatitis C Patients Treated with Interferon Alfa–2b: Another Possible Indicator of Reponse?", one page.

Choo et al., "Genetic Organization and Diversity of the Hepatitis C Virus", *Proc. Natl. Acad. Sci. USA*, vol. 88, dated Mar. 1991, pp. 2451–2455.

Choo et al., "Isolation of a cDNA Clone Derived from a Blood–Borne NOn–A, Non–B Viral Hepatits Genome", *Science*, vol. 244, dated Apr. 21, 1989, pp. 359–362.

Clemens et al., "Regulation of Cell Proliferation and Differentiation by Interferons", *Biochem*, vol. 226, dated 1985, pp. 345–360.

Costanzo–Nordin et al., "Successful Treatment of Heart Transplant Rejection with Photopheresis", *Transplantation*, vol. 53, No. 4, dated May 1992, pp. 808–815.

Dall'Amico et al., "Photopheresis in paediatric patients with drug–resistant chronic graft–versus–host disease," Brit. J. Haematol. 97: 848 (1997).

Davis et al., "Treatment of Chronic Hepatitis C with Recombinant Interferon Alfa", *The New England Journal of Medicine*, vol. 321, No. 22, dated Nov. 30, 1989, pp. 1501–1505.

Di Bisceglie et al., "Recombinant Interferon Alfa Therapy for Chronic Hepatitis C", *The New England Journal of Medicine*, vol. 321, No. 22, dated Nov. 30, 1989, pp. 1506–1510.

Dienstag, "Non–A, Non–B Hepatitis. I. Recognition, Epidemiology, and Clinical Features", *Gastroenterology*, vol. 85, No. 2, dated 1983, pp. 439–462.

Edelson et al., "Extracorporeal Photochemotherapy," Biol. Ther. Can. 4(5): 1 (1994).

Edelson, "Photopheresis: A Clinically Relevant Immunobiologic Response Modifier", *Annals of New York Academy of Sciences*, pp. 154–164.

Edelson et al., "Treatment of Cutaneous T–Cell Lymphoma by Extracorporeal Photochemotherapy", *New England Journal of Medicine*, vol. 316, No. 6, dated Feb. 5, 1987, pp. 297–303.

Edelson et al., "Treatment of Cutaneous T–Cell Lymphoma by Extracorporeal Photochemotherapy", *New England Journal of Medicine*, vol. 316, dated Feb. 5, 1987, pp. 297–304.

Farci et al., "A Long–Term Study of Hepatitis C Virus Replication in Non–A, Non–B Hepatitis", *The New England Journal of Medicine*, vol. 325, No. 2, dated Jul. 11, 1991, pp. 98–104.

Garson et al., "Enhanced Detection by PCR of Hepatitis C Virus RNA", *The Lancet*, vol. 336, dated Oct. 6, 1990, pp. 878–879.

Gil et al., "Hepatic and Extrahepatic HCV RNA Strands in Chronic Hepatitis C: Different Patterns of Response to Interferon Treatment", *Hepatology*, vol. 18, No. 5, dated Nov. 1993, pp. 1050–1054.

Gomez–Rubio et al., "Prolonged Treatment (18 months) of Chronic Hepatitis C with Recombinant α–Interferon in Comparison with a Control Group", *Journal of Hepatology*, vol. 11, dated 1990, pp. S63–S67.

Grass et al., "Inactivation of Leukocytes in Platelet Concentrates by Photochemical Treatment With Psoralen Plus UVA", *Blood*, vol. 91, No. 6, dated Mar. 15, 1998, pp. 2180–2188.

Greinix et al., "Successful Use of Extracorporeal Photochemotheragpy in the Treatment of Service Acute and Chronic Graft–Versus–Host Disease," Blood 92(9): 3098 (1998).

Hayashi et al., "Improvement of Serum Aminotransferase Levels After Phlebotomy in Patients with Chronic Active Hepatitis C and Excess Hepatic Iron", *The American Journal of Gastroeneterology*, vol. 89, No. 7, dated Jul. 1994, pp. 986–988.

Hoofnagle et al., "Treatment of Chronic Non–A, Non–B Hepatitis with Recombinant Human Alpha Interferon", *The New England Journal of Medicine*, vol. 315, No. 25, dated Dec. 18, 1986, pp. 1575–1578.

Houghton et al., "Molecular Biology of the Hepatitis C Viruses: Implications for Diagnosis, Development and Control of Viral Disease", *Hepatology*, vol. 14 No. 2, dated 1991, pp. 381–388.

Jansen et al., "Inter– and Intraindividual Variations in Serum Methoxsalen Levels During Repeated Exposure", *Current Therapeutic Research*, vol. 33, No. 2, dated Feb. 1983, pp. 258–264.

Kanai et al., "Suppression of Hepatitis C Virus RNA by Interferonα", *The Lancet*, vol. 336, p. 245.

Koretz et al., "Non–A, Non–B Posttransfusion Hepatitis—A Decade Later", *Gastroenterology*, vol. 88, No. 5, dated May 1985, pp. 1251–1254.

Lee et al., "Engineering Aspects of Extracorporeal Photochemoptherapy", *The Yale Journal of Biology and Medicine*, dated Jun. 9, 1989, pp. 621–628.

Ljunggren et al., "Plasma Levels of 8–Methoxypsoralen Determined by High–Pressure Liquid Chromatography in Psoriatic Patients Ingesting Drug from Two Manufacturers", *The Journal of Investigative Dermatology*, vol. 74, No. 1, dated Jan. 1980, pp. 59–62.

Malawista et al., "Treatment of Rheumatoid Arthritis by Extracorporeal Photochemotherapy", *Arthritis and Rheumatism*, vol. 34, No. 6, dated Jun. 1991, pp. 646–654.

Margolis–Nunno et al., "Elimination of Potential Mutagenicity in Platelet Concetrates that are Virally Inactivated with Psoralens and Ultraviolet A Light", *Transfusion*, vol. 35, No. 10, dated 1995, pp. 855–862.

Meiser et al., "Reduction of the Incidence of Rejection by Adjunct Immunosuppression With Photochemotherapy After Heart Transplantation", *Transplantation*, vol. 57, No. 4, dated Feb. 1994, pp. 563–568.

Mendoza et al., "Decreased Phorbol Myristate Acetate—Induced Release of Tumor Necrosis Factorα and Interleukin–1β from Peripheral Blood Monocytes of Patients Chronically Infected with Hepatitis C Virus", *The Journal of Intectious Diseases*, vol. 174, dated Oct. 1996, pp. 842–844.

Nakano et al., "Comparative Study of Clinical, Histological, and Immunological Responses to Interferon Therapy in Type Non–A, Non–B, and Type B Chronic Hepatitis", *The American Journal of Gastroenterology*, vol. 85, No. 1, dated Jan. 1990, pp. 24–29.

*Progress*, vol. 16, dated 1994–1995, pp. 1–12.

Qian et al., "Replication of Hepatitis C Virus in Peripheral Blood Mononuclear Cells", *Journal of Hepatology*, vol. 16, dated 1992, pp. 380–383.

Rook et al., "Combined Therapy for Sezary Syndrome with Extracorporeal Photochemotherapy and Low–Dose Interferon Alfa Therapy", dated Oct. 1991, pp. 1535–1540.

Rook et al., "Treatment of Autoimmune Disease with Extracorporeal Photochemotherapy: Pemphigus Vulgaris—Preliminary Report", *The Yale Journal of Biology and Medicine*, vol. 62, dated 1989, pp. 647–652.

Rook et al., "Treatment of Systemic Sclerosis With Extracorporeal Photochemotherapy", *Arch Dermatol*, vol. 128, dated Mar. 1992, pp. 337–346.

Rossetti et al., "Extracorporeal Photochemotherapy as Single Therapy for Extensive, Cutaneous, Chronic Graft–Versus–Host Disease", *Transplantation*, vol. 59 No. 1, dated Jan. 15, 1995, pp. 149–151.

Saez–Royuela et al., "High Doses of Recombinant α–Interferon or γ–Interferon for Chronic Hepatitis C: A Randomized, Controlled Trial", *Hepatology*, vol. 13, No. 2, dated 1991, pp. 327–331.

Shimizu et al., "Early Events in Hepatitis C Virus Infection of Chimpanzees", *Proc. Natl. Acad Sci., USA*, vol. 87, dated Aug. 1990, pp. 6441–6444.

Shindo et al., "Decrease in Serum Hepatitis C Viral RNA During Alpha–Interferon Therapy for Chronic Hepatits C", *Annals of Internal Medicine*, vol. 115, No. 9, dated Nov. 1, 1991, pp. 700–704.

Shirai et al., "Induction of Cytotoxic T Cells to a Cross–Reactive Epitope in the Hepatitis C Virus Nonstructural RNA Polymerase–Like Protein", *Journal of Virology*, dated Jul. 1992, pp. 4098–4106.

Simmonds et al., "Classification of Hepatits C Virus Into Six Major Genotypes and a Series of Subtypes by Phylogenetic Analysis of the NS–5 Region", *Journal of General Virology*, vol. 74, dated 1993, pp. 2391–2399.

Therakos, Inc., "The UVAR XTS System: Enginering That Reflects Innovation", dated Mar. 1998.

Vowels et al., "Extracorporeal Photochemotherapy Induces the Production of Tumor Necrosis Factorα by Monocytes: Implications for the Treatment of Cutaneous T–Cell Lymphoma and Systemic Sclerosis", *The Journal of Investigative Dermatology*, dated May 1992, pp. 686–692.

Watson et al., "High–Dose Interferon Alfa–2A for the Treatment of Chronic Hepatits C", *The Annals of Pharmacotherapy*, vol. 28, dated Mar. 1994, pp. 341–342.

Weiner et al., "Evidence for Immune Selection of Hepatitis C Virus (HCV) Putative Envelope Glycoprotein Variants: Potential Role in Chronic HCV Infections", *Proc. Natl. Acad. Sci., USA*, vol. 89, dated Apr. 1992, pp. 3468–3472.

Witter et al., "Effects of Prednisone, Aspirin, and Acetaminophen on an In Vivo Biologic Response to Interferon in Humans", *Clin. Pharmacol. Ther.*, vol. 44, No. 2, dated Aug. 1988, pp. 239–243.

Zic et al., "Long–term follow–up of patients with cutaneous T–cell lymphoma treated with extracorporeal photochemotherapy," J. Amer. Acad. Dermatol. 35(6): 935 (1996).

Zignego et al., "Infection of Peripheral Mononuclear Blood Cells by Hepatitis C Virus", *Journal of Hepatology*, vol. 15, dated 1992, pp. 382–386.

* cited by examiner

LOW EXTRACORPOREAL VOLUME TREATMENT SYSTEM

BACKGROUND OF THE INVENTION

1. Field of the Invention

The present invention relates to systems and apparatus that facilitate a precise process by which a batch-type process may achieve the efficiency of a continuous process, reducing the net fluid volume deficiency in a patient during a medical treatment process where fluid must be removed from a patient.

2. Description of the Prior Art

Growth in technology has allowed the medical profession to measure the precise natural fluid ratios found in the human body. Consequently, preserving these ratios during medical treatments is desirable, particularity in treatments such as photophoresis, which is discussed and claimed in U.S. Pat. No. 5,984,887 and U.S. application Ser. No. 08/832,219, which are expressly incorporated herein by reference. By way of example, a photophoresis process such as the UVAR® process (Therakos, Inc., West Chester, Pa.) removes blood from a patient, separates the buffy coat from the plasma and red blood cells and replaces the biological fluids in a batch process. When blood is removed from the patient, however, a volume deficit is created within the patient. This volume deficit is particularly detrimental in small children and the elderly or in patients that suffer from certain illnesses or diseases because their blood has a higher percentage of plasma relative to the cellular components. This volume imbalance requires that a greater volume of blood be drawn from the patient to obtain the required amount of red blood cells. This especially impacts infants and sick children who may have low body weight and hemocrit percentages of 25–30% which is significantly lower than the normal average of 45%. The need thus arose to be able to detect small incremental changes in natural fluid ratios within the body and to use these measurements to create a process by which the net fluid volume collected or removed from a patient may be reduced during-a medical treatment process.

SUMMARY OF THE INVENTION

The objects of the present invention include providing systems and apparatus for increasing the efficiency of a continuous process through a modified batch-type process, using a biological fluid and one or more centrifuge bowls to reduce the net fluid volume deficiency in a patient during a medical treatment process. An additional object may be to alleviate the difficulty in finding multiple proper insertion sites by requiring only one insertion site.

The present invention solves the inadequacies of the prior art by being able to detect small incremental changes in fluid volumes and by achieving the results of a continuous process. An efficient batch process or other Latham bowl batch-type technique is used to simulate a continuous process by which fluid is continually added and removed from a patient to account for any net fluid volume deficiency at any point in time within a medical treatment process and yet achieve higher separation and treatment efficiencies than, for example, a continuous flow separation treatment.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the present invention may include, in one or more embodiments, a method, apparatus, and system, and in a preferred embodiment an automated system, for reducing the net fluid volume change of a biological fluid within a patient during a treatment cycle by determining the net fluid volume change in the patient, adjusting the net fluid volume deficiency in the patient to obtain a minimal net fluid volume deficiency, and maintaining a minimal net fluid volume deficiency.

Additionally, determining the net fluid volume deficiency may be achieved through the use of a load cell, designed to measure the change in weight of a storage chamber. Adjusting the net fluid volume deficiency to obtain a minimal net fluid volume deficiency may involve increasing or decreasing the amount of biological fluid returned to a patient through use of a valving means and/or a pumping means to adjust the flow of a biological fluid. Maintaining the net fluid volume deficiency may also involve using one or more of the following: a load cell, pumping means, and valving means. Maintaining a minimal net fluid volume deficiency may also involve monitoring the net fluid volume deficiency.

The automation of the system may be accomplished by a computer system. Such a system may comprise a computer processor with memory which is coupled to the computer processor, and a computer process that is stored in the memory that includes obtainers and controllers configured to obtain, adjust and maintain a minimal net fluid volume deficiency. The obtainer may be associated with a load cell and the controllers may be associated with valving means and/or pumping means designed to adjust the minimum net fluid volume deficiency. The pumping means may be designed to increase or decrease the flow of biological fluids to be delivered to a patient.

Alternatively, the system for determining, adjusting, and maintaining the minimal net fluid volume deficiency may be a controller that communicates with the load cell, valving means, and pumping means. This controller may be a computer that controls the load cell, valving means, and pumping means.

In an alternative embodiment, the biological fluid may be primer fluid. Preferably, the primer fluid may contain red blood cells, plasma, or red blood cells and plasma.

It is understood that both the foregoing general description and the following detailed description are exemplary and explanatory only and are not restrictive of the invention as claimed. The accompanying drawings illustrate several embodiments of the invention and together with the description serve to explain the principles of the invention.

DETAILED DESCRIPTION OF THE PREFERRED EMBODIMENTS

Reference will now be made in detail to the present preferred or exemplary embodiments of the invention, examples of which are illustrated in the accompanying drawings.

In a specific embodiment, the present invention relates to methods, apparatus, and systems that facilitate a process which reduces the net volume of a biological fluid removed from a patient during a medical treatment process. Biological fluids encompass fluids that comprise, exist in, or are used in or delivered to living organisms. Indeed, biological fluids may comprise bodily fluids and their components, such as blood cells, plasma, and other fluids that comprise biological components, including living organisms such as bacteria, cells, or other cellular components. Biological fluids may also comprise whole blood or specific whole blood components, including red blood cells, platelets, white blood cells, and precursor cells. In particular, it may be desirable to remove blood from a patient without creating a volume deficit within the patient in situations where a patient may have low body weight or lower hemocrit percentages than normal. Pumping primer fluid into the patient as blood is removed or recycling the red blood cell and plasma portions of the blood back into the patient reduces the net fluid volume deficiency. The primer fluid may comprise a saline solution, blood components or other biocompatible or sterile fluids with compositions, osmolality, and viscosities similar to those of biological fluids.

Figure 1:
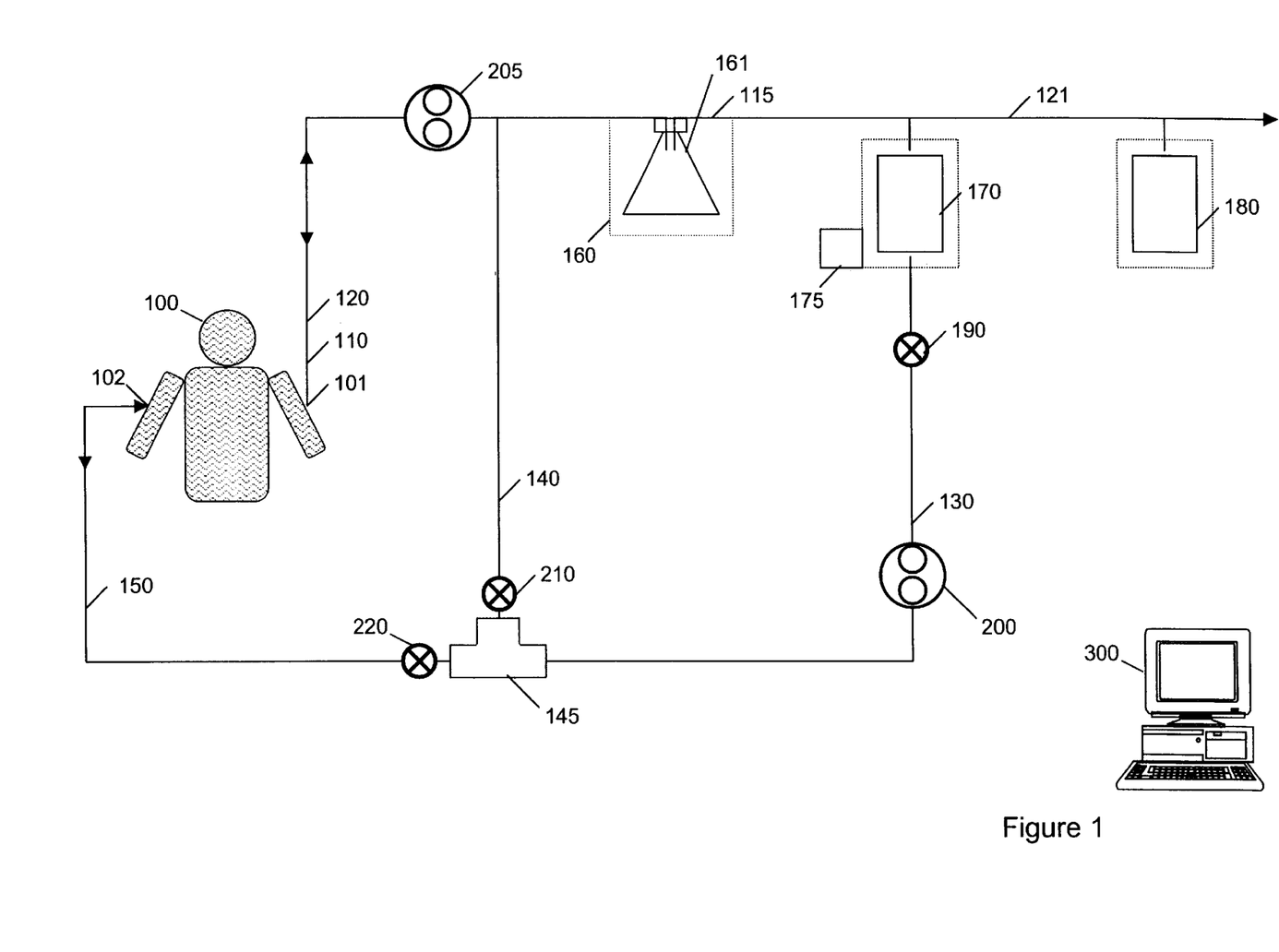
FIG. 1 is a schematic diagram of a specific embodiment of a low extracorporeal volume system.

To achieve the objects and in accordance with the purpose of the invention, as embodied and broadly described herein, for example, FIG. 1 depicts a specific embodiment of the invention. The embodiment of the present invention depicted in FIG. 1 comprises a first line 120 connected to a patient 100. Line 120 may comprise a conventional intravenous ("IV") line or cannula and associated needle, which is used to remove blood from a patient 100 at first insertion site 101. The line 120 is preferably in fluid communication with a centrifuge 160 which is preferably operable at a speed of 4800 rpm +/-5%.

Additionally, a pumping means 205 may be located on line 120 to assist in drawing blood from patient 100. This pumping means 205 may be any type of pump, such as, for example, a peristaltic pump or Kamen type pump. Pumping means 205 preferably has a range of 0 to 150 ml/min with flow accuracy of +/-10 ml/min.

Blood 110 flows from the patient 100 through line 120 to centrifuge 160. Centrifuge 160 is located on and is in fluid communication with line 120 and contains a centrifuge bowl 161 that separates the buffy coat from the other components of the blood. The centrifuge bowls are preferably disposable bowls, which are most preferably capable of containing 125 ml of fluid. The buffy coat is transferred from centrifuge bowl 161 and is stored in buffy coat chamber 180, which is located on and in fluid communication with line 121, where it awaits photophoresis treatment. Line 121 is preferably made of sterile material, similar to that used for line 120, and connects line 120 to buffy coat chamber 180. Buffy coat chamber 180 is preferably a sealed flexible sterile chamber which preferably has associated with it means to add or remove fluids. Plasma 115 flows out of centrifuge 160 into line 130, which preferably extends from and is in fluid communication with line 120 and is in fluid communication with storage chamber 170. Both lines 120 and 130 may be made of any type of flexible or rigid tubing (such as medical tubing) or other such device providing a sealed passageway for the flow of fluids into or out of a reservoir of any sort, and which preferably can be disposable and sterilizable. Storage chamber 170 is preferably a flexible sterile chamber which has a means to add or remove fluids, such as for example the red blood cells captured by centrifuge 160, and stores the separated red blood cells and plasma. Storage chamber 170 may also be used to contain a primer (e.g. blood, packed cells, anti-coagulant, saline, albumin, etc.) that can be pumped by pumping means 200 into the patient 100.

Load cell 175 is associated with storage chamber 170, associated with line 130. Load cell 175 can be a strain gauge type load cell or any type of load cell that is designed to weigh volumes of fluid. Load cell 175 is associated with and measures the weight of storage chamber 170 and may provide feedback to control system 300. Also located on line 130 is valving means 190. Valving means 190 controls the flow of plasma and red blood cells out of storage chamber 170.

Pumping means 200 is located on and in fluid communication with line 130 and may be any type of pump such as, for example, a peristaltic pump or Kamen type pump that is constructed of appropriate material to pump biological fluids and maintain the sterility of the system and is preferably of a type that allows continuous fluid flow from storage chamber 170 through lines 130, 140 and 150 into the patient 100. The pumping means is preferably used to draw primer fluid from storage chamber 170 and pump primer fluid at the appropriate rate, which is dependant on the amount of fluid needed to reduce the net fluid volume deficiency, into a patient. Alternatively, a continuous flow type pumping means may be used instead of pumping means 200, such as, for example the inclusion of rigid chambers as disclosed in U.S. Pat. No. 4,573,992, disposed about chambers 170 and 180. Pumping means 200 preferably has a range of 0 to 150 ml/min with flow accuracy of +/-10 ml/min. Pumping means 200 is adapted to pump primer fluid, including red blood cells and plasma, through line 130 to conduit juncture 145.

Figure 2:
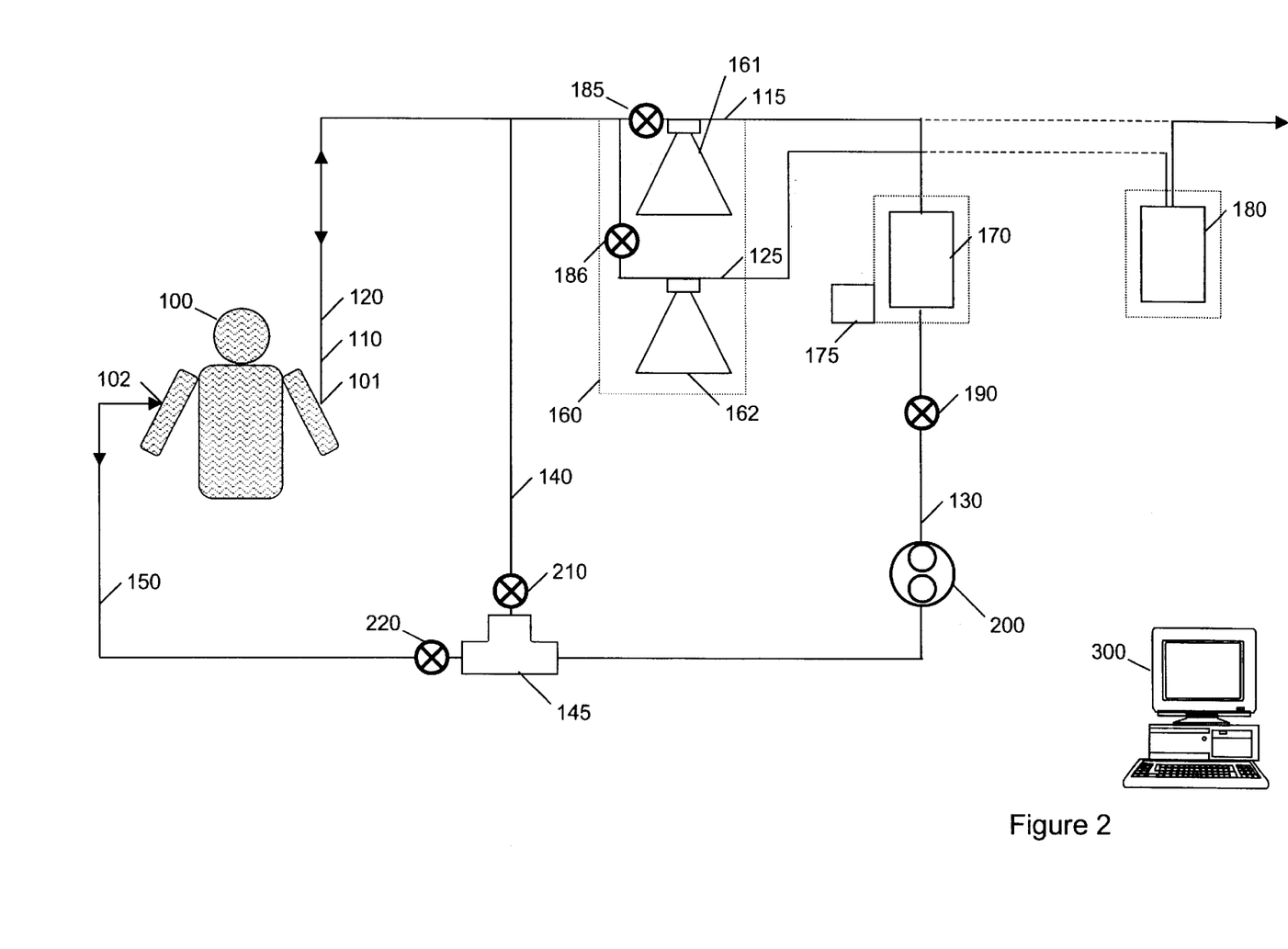
FIG. 2 is a schematic diagram of an alternative embodiment of a low extracorporeal volume system that utilizes multiple centrifuge bowls.

Conduit juncture 145 joins lines 130, 140 and 150, is preferably made of a sterile material, similar to that used for lines 120 and 130, and may be y-shaped. Line 140 is in fluid communication with line 120 and conduit juncture 145. A valving means 210 which may be, for example, a solenoid valve or any other type of valve capable of maintaining the sterility of bodily fluids, is located on line 140 and controls the flow of blood 110 between lines 120 and line 130 as shown in FIGS. 1 and 2. Line 150 is in fluid communication with conduit juncture 145 and patient 100 and may be made of the same material as lines 130 and 140 and may comprise a conventional IV line or cannula and associated needle that connects to a patient 100 at second insertion site 102. A valving means 220 is located on line 150 and is in fluid communication with conduit juncture 145 and patient 100. Valving means 220 controls the flow of fluids (e.g., blood, plasma, red blood cells, or primer fluid) to patient 100.

In a particular embodiment of the present invention, there may be a pause in the process, preferably a very slight pause. This pause occurs if the flow of blood from a patient must be stopped to allow the red blood cells and/or buffy coat to be emptied from a full centrifuge bowl 161 into storage chamber 170 and/or buffy coat chamber 180, respectively. In an alternative embodiment, the pause in the treatment process caused by emptying the red blood cells in centrifuge bowl 161 into storage chamber 170 may be eliminated by implementing additional centrifuge bowls as illustrated in FIG. 2, which addition allows the flow of blood to continue into the additional centrifuge bowl(s) while first centrifuge bowl 161 is emptied. A valving means 185 is located on line 120 before centrifuge bowl 161 and is used to control the flow of blood 110 into first centrifuge bowl 161. A second centrifuge bowl 162 is placed in a parallel combination with centrifuge bowl 161 on line 125. A valving means 186 is located on line 125 before second centrifuge bowl 162 and is used to control the flow of blood 110 into second centrifuge bowl 162. When first centrifuge bowl 161 is ready to be emptied into storage chamber 170, valving means 185 shuts, causing blood 110 to flow into line 125. Blood 110 flows through line 125 into second centrifuge 162, which then separates the blood into its components. When second centrifuge bowl 162 is ready to be emptied into storage chamber 170, valving means 186 shuts and valving means 185 opens, causing blood 110 to flow into first centrifuge bowl 161.

Centrifuge bowls may be emptied in any acceptable means such as, for example, by providing a vacuum whereby the contents of a centrifuge bowl are drawn into a chamber and the contents are replaced by sterile air from another chamber or any other acceptable source. For example, in the system depicted by FIG. 2, sterile air can be provided from either storage chamber 170 or buffy coat chamber 180 and the vacuum could be drawn from the remaining chamber on the centrifuge bowl. An additional conduit or conduits, such as, for example, between storage chamber 170 and first centrifuge bowl 161, may be provided for an additional or separate path for this flow of air and chamber contents.

In yet another alternative embodiment, only one insertion site is needed. This is useful in situations where a small child or elderly person, due to the symptoms and effects of their illness, have weak or collapsed veins that make drawing blood through an IV difficult. As demonstrated in FIG. 3, a one-needle configuration can be used to alleviate the difficulty in finding a proper insertion site. A dual cannula needle, for example, may be used for this embodiment that is in fluid communication with insertion site 101 and line 120. Blood 110 flows through the first cannula of the IV needle and through line 120 into centrifuge 160. Once primer fluid is needed to prevent or correct a net volume deficiency within a patient, as indicated by load cell 175, the system and apparatus work similarly to the embodiment described above, until the fluid passes through pumping means 200.

Figure 3:
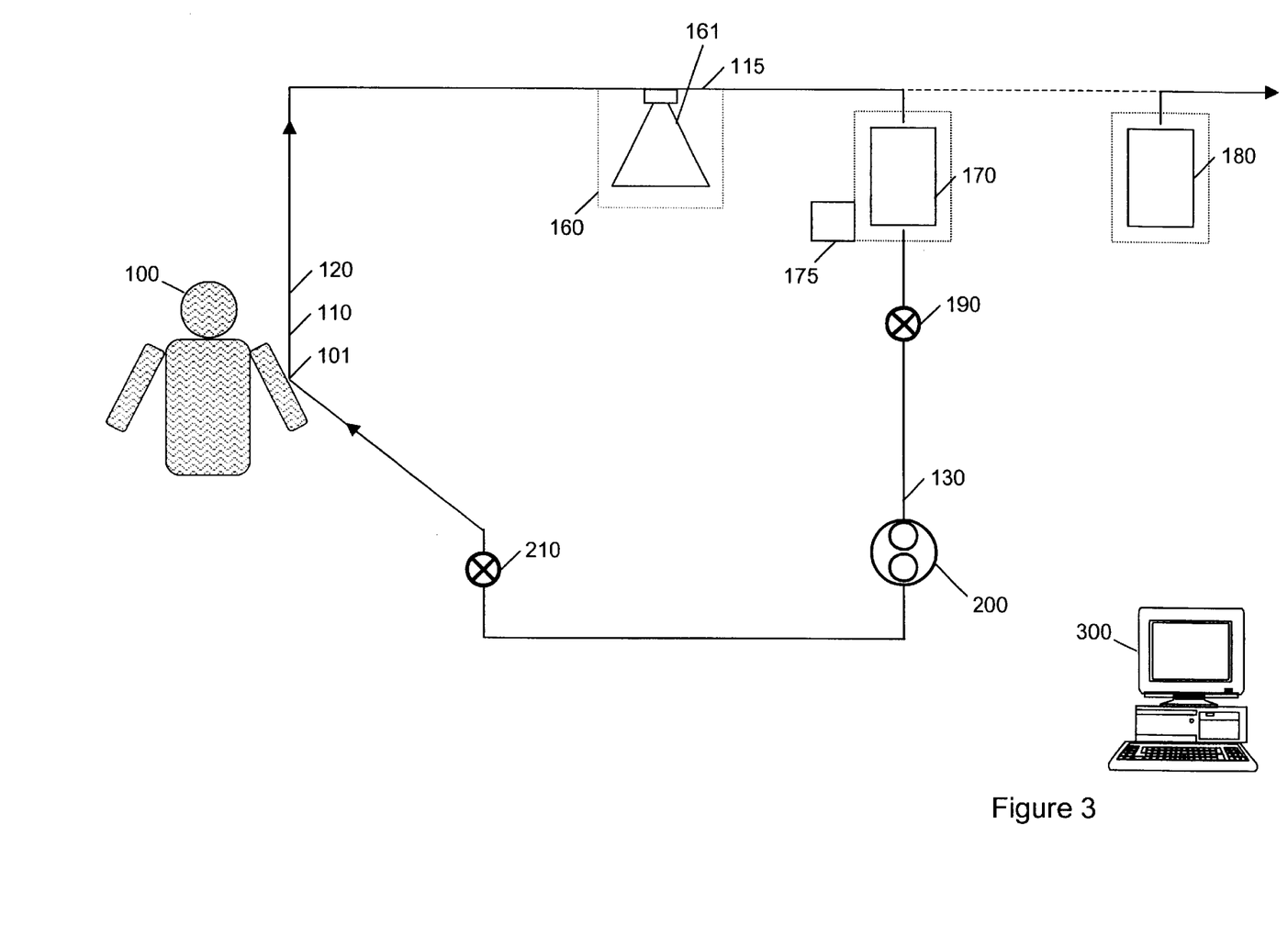
FIG. 3 is a schematic diagram of an alternative embodiment of a low extracorporeal volume system in a one-needle configuration.

After the biological fluid flows through pumping means 200, it continues through line 130. Valving means 210 is in fluid communication with line 130 and is used to regulate the flow of the fluid back into patient 100. The fluid enters patient 100 through the second cannula of the IV needle at insertion site 101.

Figure 4:
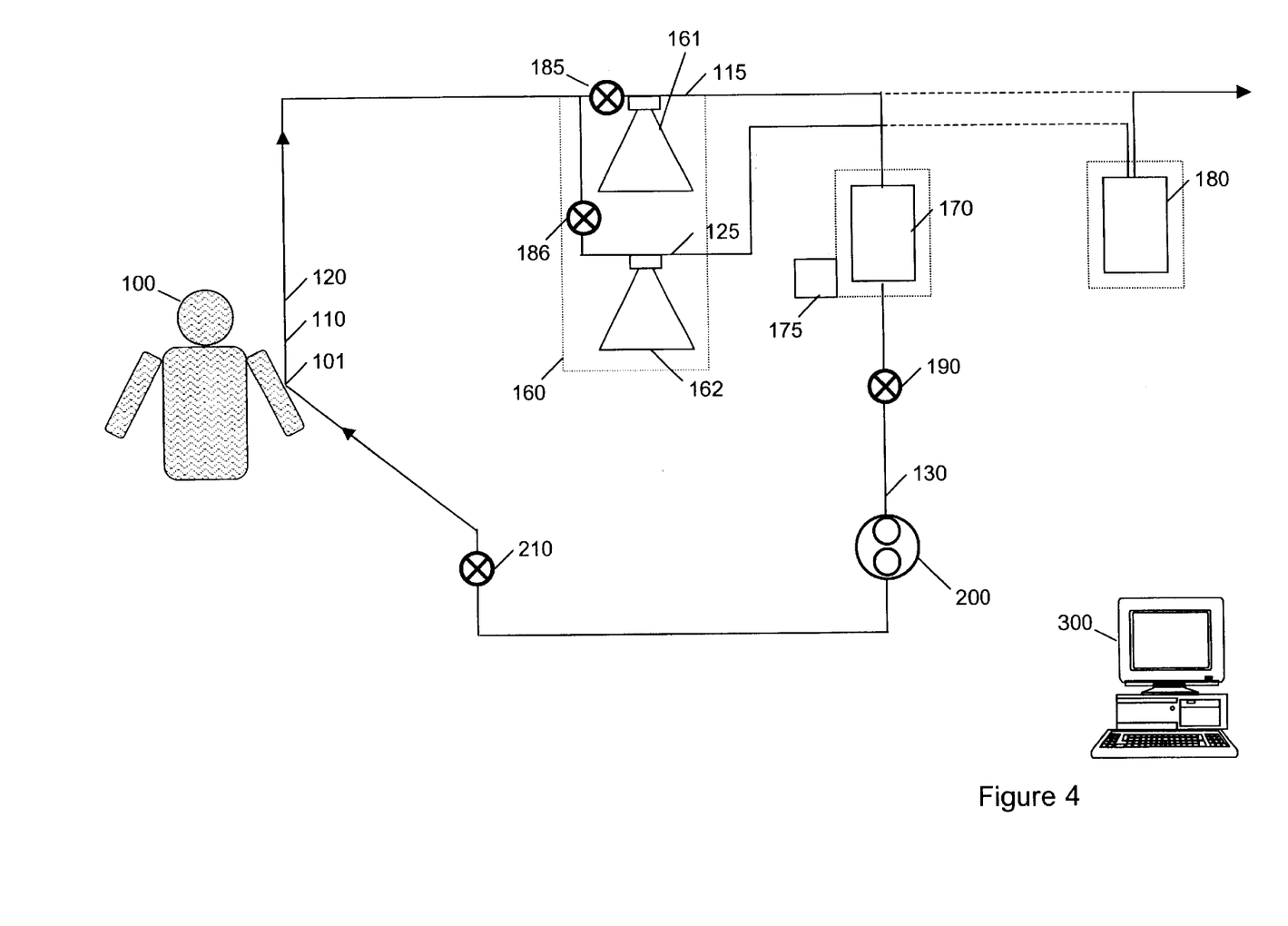
FIG. 4 is a schematic diagram of an alternative embodiment of a low extracorporeal volume system that utilizes multiple centrifuge bowls in a one-needle configuration.

FIG. 4 depicts another alternative embodiment of the present invention which eliminates the pause in the treatment process caused by emptying the red blood cells from centrifuge bowl 161 into storage chamber 170 in the same manner as FIG. 2. FIG. 4, in contrast to FIG. 2, is in a one-needle configuration, like FIG. 3, which may be used to alleviate the difficulty in finding proper insertion sites. Oftentimes, as a result of an illness, a patient's veins may be weak or collapsed which may make drawing or distributing blood into the vein difficult. The difficulty in finding a strong vein is increased when more than one vein is needed.

Figure 5:
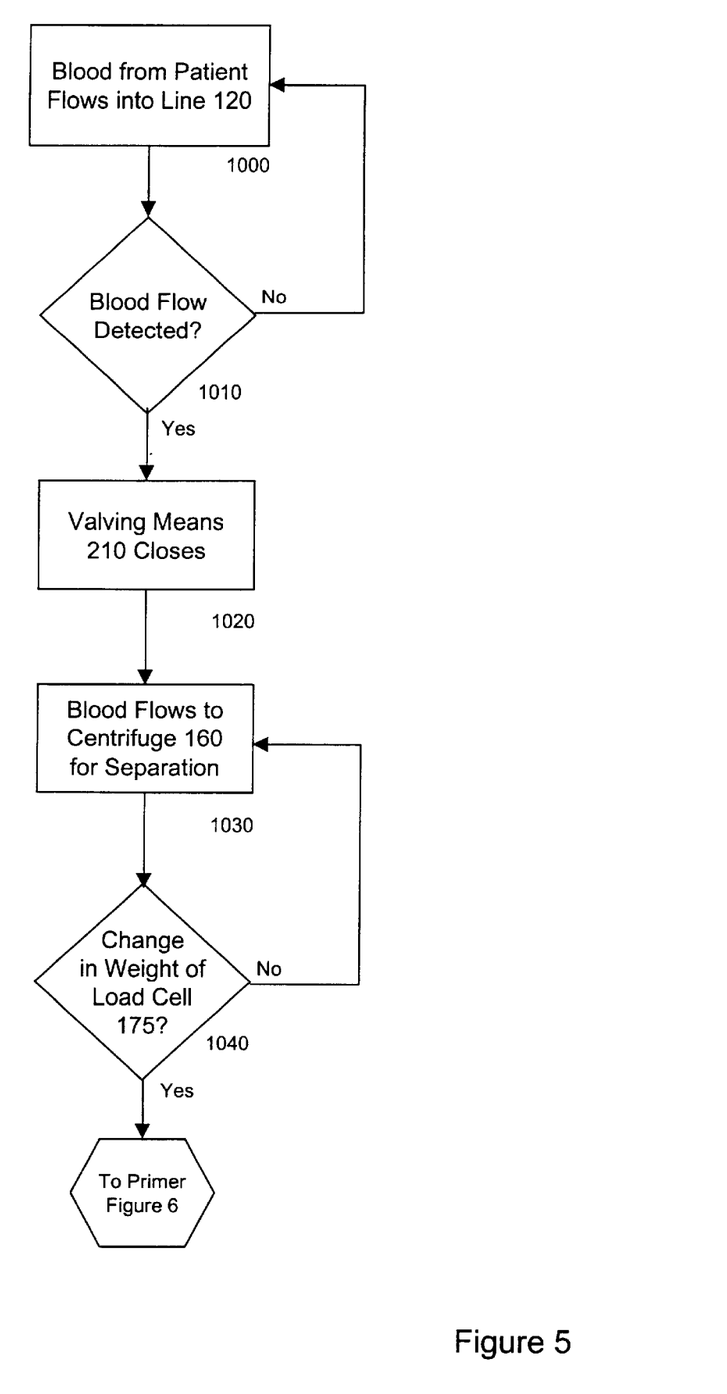
FIG. 5 is a flowchart diagram of the blood removal and transportation process for use in low extracorporeal volume systems.
Figure 6:
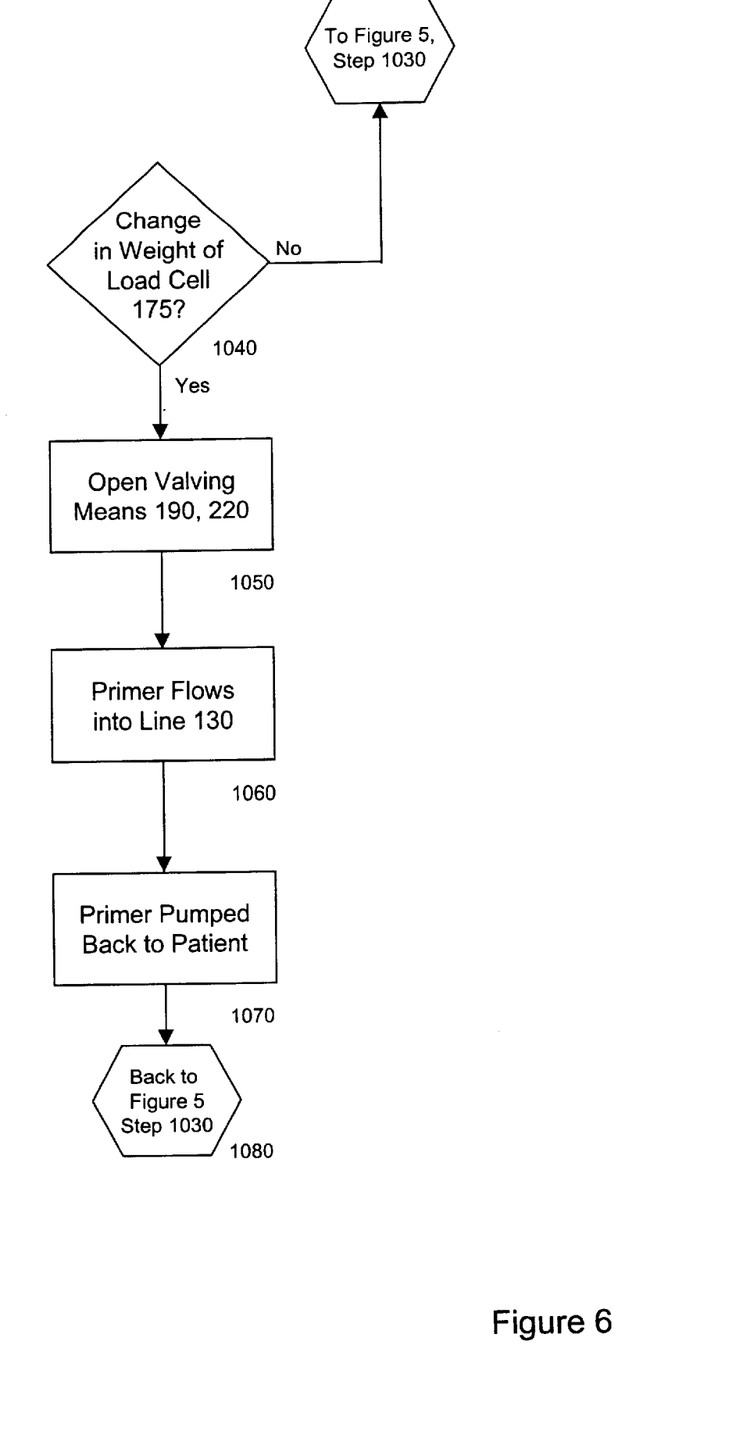
FIG. 6 is a flowchart diagram of the priming process for use in low extracorporeal volume systems.

FIGS. 5 and 6 are flowchart diagrams that depict the blood removal and transportation portion of an embodiment of the present invention. First, in step 1000, blood is collected from the patient 100 via the first insertion site 101 and flows into line 120. If the presence of blood is visually or electronically detected within line 120 in step 1010, valving means 210 closes in step 1020. Blood then flows into centrifuge 160 to be separated by centrifuge bowl 161 into the three required components (plasma, red blood cells, and buffy coat) in step 1030. Plasma 115 preferably automatically flows out of centrifuge 160 into storage chamber 170. The buffy coat and red blood cells remain in centrifuge bowl 161 until centrifuge bowl 161 is full and the components are manually removed. Upon removal, the buffy coat is emptied into buffy coat chamber 180 where it awaits treatment. The red blood cells are emptied into storage chamber 170.

In step 1040, load cell 175 measures the weight of storage chamber 170. Any change in the weight of storage chamber 170 indicates a net volume change within the patient. If the weight of storage chamber 170 changes positively, valving means 190 and 220 are opened in step 1050. In step 1060, the fluid contained in storage chamber 170 is pumped according to the incremental change in weight of storage chamber 170, as shown by load cell 175, into line 130. In step 1070, primer is pumped by pumping means 200 through conduit juncture 145 and valving means 220, and returns to the patient via line 150 and second insertion-site 102. If the weight of storage chamber 170 changes negatively, valving means 190 closes and fluid is collected in storage chamber 170 until there is a positive change in the weight of storage chamber 170, indicating that there may be a net fluid volume deficiency in the patient.

The above system mechanisms are preferably operated by a digital control system 300 that provides a means of electronically activating valving means 190, 210, 220 and pumping means 200 and may also include electronic circuitry and a microprocessor coupled to any necessary indicators and including an input for command control signals. Control system 300 may also receive and transmit data to and from possible pressure indicators, flow indicators, valving means, microprocessors, and any other electronic data transport means and may be configured in various ways depending upon the degree of control and information needed in a particular application.

Control system 300 is optionally arranged to monitor the entire process and obtain data regarding the level of fluid dispensed to the patient. The user may then download information for statistical analysis and obtain system diagnostics information for maintenance and repair purposes. This arrangement may include a setup program that allows the user to modify various variables that will be used by the control system in determining net fluid volume deficiency, mechanism calibration, error tolerances, etc. The arrangement may also provide a means to automate or direct a user in the preliminary calibration of any relevant instrumentation.

The microprocessor is preferably able to control many treatment parameters simultaneously. Functions that are critical to a medical treatment process are preferably redundantly monitored with back-up circuits. The in-process memory may retain information on treatment parameters in a battery-packed memory to enable the continuation of the medical treatment process in the event of a transient power loss. All communications between control system 300 and the mechanical system are preferably centralized with positive action buttons and an alphanumeric message center. Microprocessor-controlled fluid volumes collected and distributed are preferably clearly displayed. Controls may be arranged so that the medical treatment process phase is visible at a glance.

This control system 300 and its operation may be monitored and controlled remotely, including via communication through modem connection by telephone lines or via the internet. Additionally, data related to patient conditions or medical treatment processes may be downloaded for use as direct input for control system 300 via Internet or any other network system connection.

Other embodiments of the invention will be apparent to those skilled in the art from consideration of the specification and the practice of the invention disclosed herein. It is intended that the specification and examples be considered as exemplary only, with a true scope and spirit of the invention being indicated by the following claims.

What is claimed is:

1. A method for reducing a net fluid volume change of a biological fluid in a patient during a photophoresis process, comprising the steps of:
   removing said biological fluid from said patient;
   determining said net fluid volume change in said patient;
   adjusting said net fluid volume change of said patient so that a minimum net fluid volume deficiency is obtained, wherein said adjusting step comprises adding fluid to said patient both at a point in time during which said biological fluid is being removed from said patient and at a point in time during which said biological fluid is not being removed from said patient; and
   maintaining said minimum net fluid volume deficiency in said patient after said adjusting step.

2. The method of claim 1, wherein said determining said net fluid volume change comprises measuring the change in weight of a chamber associated with a load cell.

3. The method of claim 1, wherein said adjusting said net fluid volume change comprises decreasing said fluid added to said patient.

4. The method of claim 3, wherein said fluid comprises a primer fluid.

5. The method of claim 4, wherein said primer fluid further comprises red blood cells and plasma.

6. The method of claim 4, wherein said primer fluid further comprises red blood cells.

7. The method of claim 4, wherein said primer fluid further comprises plasma.

8. The method of claim 1, wherein said adjusting said net fluid volume change comprises increasing said fluid added to said patient.

9. The method of claim 8, wherein said fluid comprises a primer fluid.

10. The method of claim 9, wherein said primer fluid further comprises red blood cells and plasma.

11. The method of claim 9, wherein said primer fluid further comprises red blood cells.

12. The method of claim 9, wherein said primer fluid further comprises plasma.

13. The method of claim 1, wherein said adjusting of said net fluid volume change comprises controlling a valving means to change a flow rate of a fluid.

14. The method of claim 1, wherein said adjusting of said net fluid volume change comprises controlling a pumping means used to change a flow rate of a fluid.

15. The method of claim 14, wherein said adjusting of said net fluid volume change comprises controlling said pumping means so that said flow rate is increased.

16. The method of claim 14, wherein said adjusting of said net fluid volume change comprises controlling said pumping means so that said flow rate is decreased.

17. The method of claim 14, wherein said fluid comprises a primer fluid.

18. The method of claim 17, wherein said primer fluid further comprises red blood cells and plasma.

19. The method of claim 17, wherein said primer fluid further comprises red blood cells.

20. The method of claim 17, wherein said primer fluid further comprises plasma.

21. The method of claim 13, wherein said adjusting of said net fluid volume change comprises controlling said valving means so that said flow rate is increased.

22. The method of claim 13, wherein said adjusting of said net fluid volume change comprises controlling said valving means so that said flow rate is decreased.

23. The method of claim 13, wherein said fluid comprises a primer fluid.

24. The method of claim 23, wherein said primer fluid further comprises red blood cells and plasma.

25. The method of claim 23, wherein said primer fluid further comprises red blood cells.

26. The method of claim 23, wherein said primer fluid further comprises plasma.

27. The method of claim 1, wherein said maintaining step comprises monitoring said net fluid volume change to regulate said minimum net fluid volume deficiency.

28. A system for regulating a photophoresis process for reducing a net fluid volume change in a patient, comprising:
   means for removing biological fluid from said patient;
   means for determining said net fluid volume change in said patient;
   means for adjusting said net fluid volume change of said patient so that a minimum net fluid volume deficiency is obtained, wherein said means for adjusting is adapted to add fluid to said patient both at a point in time during which said biological fluid is being removed from said patient and at a point in time during which said biological fluid is not being removed from to said patient; and
   means for maintaining said minimum net fluid volume deficiency in said patient after said adjusting.

29. The method of claim 23, wherein said means for determining said net fluid volume change in said patient comprises a load cell.

30. The system of claim 28, wherein said means for adjusting said net fluid volume change comprises a valving means.

31. The system of claim 28, wherein said means for adjusting said net fluid volume change comprises a pumping means for increasing or decreasing the flow of a fluid.

32. The system of claim 31, wherein said fluid comprises a primer fluid.

33. The system of claim 32, wherein said primer fluid further comprises red blood cells and plasma.

34. The system of claim 32, wherein said primer fluid further comprises red blood cells.

35. The system of claim 32, wherein said primer fluid further comprises plasma.

36. The system of claim 28, wherein said means for adjusting said net fluid volume change comprises a valving means for increasing or decreasing the flow of a fluid.

37. The system of claim 36, wherein said fluid comprises a primer fluid.

38. The system of claim 37, wherein said primer fluid further comprises red blood cells and plasma.

39. The system of claim 37, wherein said primer fluid further comprises red blood cells.

40. The system of claim 37, wherein said primer fluid further comprises plasma.

41. The system of claim 28 wherein:

said means for determining said net fluid volume change in said patient comprises a load cell;

said means for adjusting said net fluid volume change of said patient comprises a load cell, pumping means and a valving means; and said means for maintaining said minimum net fluid volume deficiency in said patient comprises a load cell, pumping means, and a valving means.

42. The system of claim 41, wherein said means for adjusting said net fluid volume change further comprises a controller in communication with said load cell, said valving means, and said pumping means, and controller comprising a computer that regulates and controls said load cell, said valving means, and said pumping means.

43. The system of claim 41, wherein said means for maintaining said minimum net fluid volume deficiency further comprises a controller in communication with said load cell, said valving means, and said pumping means, said controller comprising a computer that regulates and controls said load cell, said valving means, and said pumping means.

44. A system for regulating a photophoresis process for reducing a net fluid volume change in a patient, comprising:

a first line configured to transport a biological fluid from a patient;

at least one centrifuge connected to said first line for separating said biological fluid into a first part and a second part;

storage chamber configure to receive said first part;

a second line configured to transport said first part, said second line in fluid communication with said centrifuge and said storage chamber;

a load cell configured to weigh the contents of said storage chamber;

a third line configured to transport said first part from said storage chamber to said patient;

a pump disposed within said third line;

a valve disposed within said third line; and a controller in communication with said load cell, said pump, and said valve, said controller comprising a computer configured to regulate and controls said load cell, said pump, and said valve.

45. The system of claim 44 further comprising a plurality of centrifuges.

46. The system of claim 45 further comprising at least one valve in said first line configured to allow said first line to be in fluid communication with any one of said plurality of centrifuges.

47. The system of claim 44 wherein said first part comprises plasma.

48. The system of claim 44 wherein said first part comprises red blood cells.

49. A system for regulating a photophoresis process for reducing a net fluid volume change in a patient, comprising:

a first line configured to transport a biological fluid from a patient;

at least one centrifuge connected to said first line for separating said biological fluid into a first part and a second part;

a storage chamber configured to receive said first part;

a second line configured to transport said first part, said second line in fluid communication with said centrifuge and said storage chamber;

a load cell configured to weigh the contents of said storage chamber;

a third line configured to transport said first part form said storage chamber to said patient;

a pump disposed within said third line;

a valve disposed within said third line;

a controller in communication with said load cell, said pump, and said valve, said controller comprising a computer configured to regulate and controls said load cell, said pump, and said valve; and a dual cannula needle having a first cannula and a second cannula, wherein said first line is connected to said first cannula and said second line is connected to said second cannula.

* * * * *

UNITED STATES PATENT AND TRADEMARK OFFICE
CERTIFICATE OF CORRECTION

PATENT NO. : 6,793,643 B1
DATED : September 21, 2004
INVENTOR(S) : Dennis A. Briggs It is certified that error appears in the above-identified patent and that said Letters Patent is hereby corrected as shown below:

Title page,
Item [56], References Cited, OTHER PUBLICATIONS, at "Margolis-Nunno et al.", reference, please "Concetrates" and insert -- Concentrates -- therefore.
"Mendoza et al.,", reference, please delete "Factorα" and insert -- Factor-α -- therefore
"Vowels et al.", reference, please delete "Factorα" and insert -- Factor-α -- therefore.

Column 9,
Line 36, please delete "configure" and insert -- configured --; therefore.

Column 10,
Line 31, please delete "form" and insert -- from -- therefore.

Signed and Sealed this

Fifth Day of April, 2005

JON W. DUDAS
*Director of the United States Patent and Trademark Office*